United States Patent
Lorenzo

(10) Patent No.: US 8,636,988 B2
(45) Date of Patent: Jan. 28, 2014

(54) COMPOSITION FOR TREATMENT OF SUNBURNED SKIN

(75) Inventor: Angela L. Lorenzo, North Las Vegas, NV (US)

(73) Assignee: Doctor Essentials, North Las Vegas, NV (US)

( * ) Notice: Subject to any disclaimer, the term of this patent is extended or adjusted under 35 U.S.C. 154(b) by 855 days.

(21) Appl. No.: 12/364,336

(22) Filed: Feb. 2, 2009

(65) Prior Publication Data

US 2009/0196840 A1  Aug. 6, 2009

Related U.S. Application Data

(60) Provisional application No. 61/025,036, filed on Jan. 31, 2008.

(51) Int. Cl.
  *A61K 8/00* (2006.01)
  *A61Q 19/00* (2006.01)
  *A61Q 17/04* (2006.01)
  *A61K 45/00* (2006.01)
  *A61K 31/573* (2006.01)

(52) U.S. Cl.
  CPC ............... *A61K 45/00* (2013.01); *A61K 31/573* (2013.01); *Y10S 514/828* (2013.01)
  USPC .......... 424/59; 424/78.06; 424/642; 424/744; 514/828

(58) Field of Classification Search
  CPC ............................. A61K 45/00; A61K 31/573
  USPC .................. 424/59, 78.06, 642, 744; 514/828
  See application file for complete search history.

(56) References Cited

U.S. PATENT DOCUMENTS

| | | |
|---|---|---|
| 4,474,753 A | 10/1984 | Haslam et al. |
| 4,959,205 A | 9/1990 | Brunner et al. |
| 5,558,914 A | 9/1996 | Cohen et al. |
| 5,614,178 A | 3/1997 | Bloom et al. |
| 5,674,912 A | 10/1997 | Martin |
| 5,709,847 A | 1/1998 | Bissett et al. |
| 5,948,416 A | 9/1999 | Wagner et al. |
| 5,961,997 A | 10/1999 | Swinehart |
| 6,444,647 B1 | 9/2002 | Robinson et al. |
| 7,037,513 B1 | 5/2006 | Traynor et al. |
| 2006/0105000 A1* | 5/2006 | Friedman ................. 424/400 |
| 2008/0025922 A1* | 1/2008 | Marrs ................... 424/47 |
| 2009/0143458 A1* | 6/2009 | Jensen et al. ............. 514/423 |
| 2009/0269289 A1* | 10/2009 | Sredni et al. ............. 424/59 |

OTHER PUBLICATIONS

Allenby, et al., "Perinal—a new no-touch spray to relieve the symptoms of pruritus ani.", Int. J. Colorectal Dis., vol. 8, No. 4, pp. 184-187, Abstract (1993).
http://www.sascoproducts.com/products/82, "Aloe Intensive Medi-Aid Ointment with A, D & E", Sasco Products, at least as early as Aug. 25, 2006.
Midwood, et al., "Tissue repair and the dynamics of the extracellular matrix", The International Journal of Biochemistry & Cell Biology, 36 (6): 1031-1037 (2004).
Chang et al., "Gene Expression signature of fibroblast serum response predicts human cancer progression: similarities between tumors and wounds", PLoS biology 2 (2): E7 (2004).

* cited by examiner

*Primary Examiner* — Mina Haghighatian
(74) *Attorney, Agent, or Firm* — Workman Nydegger

(57) ABSTRACT

A composition for treatment of burned or irritated skin. The composition includes an anesthetic component comprising lidocaine, an anti-inflammatory component comprising hydrocortisone, an emollient comprising aloe vera, and a pharmaceutically acceptable base. The resulting composition has a cream like consistency. Upon application to the skin, there is no slimy or sticky residue, but the composition becomes nearly dry to the touch. It exhibits a smooth, silk like feel once applied. When applied to an area of burned or irritated skin, the pain immediately subsides, and in the case of sunburn, there is a noticeable tendency for the composition to reduce or eliminate peeling of the skin as the sunburn heals.

5 Claims, No Drawings

COMPOSITION FOR TREATMENT OF SUNBURNED SKIN

RELATED APPLICATIONS

The present application claims the benefit of U.S. Provisional Patent Application Ser. No. 61/025,036, filed Jan. 31, 2008, and entitled "COMPOSITION FOR TREATMENT OF SUNBURNED SKIN", the disclosure of which is incorporated in its entirety.

BACKGROUND OF THE INVENTION

1. The Field of the Invention

The present invention is directed to compositions for treatment of skin. More particularly, the present invention is directed to compositions for relief of burned or irritated skin.

2. The Relevant Technology

It is now believed that chronic exposure to sunlight is detrimental to human skin. Although exposure typically results in a tan, having an aesthetically appealing appearance, it is now known that the tanning process damages the skin. In mild cases, this damage may cause increased creasing and wrinkling of the dermis, irregular thickening and thinning, yellowing and drying: in short, "premature aging." More extreme acute exposure to sunlight often causes acute erythema and inflammation (commonly referred to as sunburn)

Protection from damage due to sunlight traditionally comprises clothing over most of the body, with occasional application of a sunscreen or sunblock formulation during periods of greater exposure. Sunscreens are chemicals which absorb UV radiation in the hazardous wavelength range, and are generally water-soluble. Sunscreens generally absorb only a fraction of the incident UV radiation, and allow some UV to pass through. The proportion of UV absorbed is reported as the "sun protection factor" or SPF, and indicates the factor by which one may increase one's exposure to sunlight without burning. Strictly speaking, a sunblock is generally a formulation opaque to UV, typically containing titanium dioxide or zinc oxide, which stops essentially all light from reaching the skin.

Even when taking care to avoid over exposure to sunlight, many people still experience sunburn. Nearly everyone has such experience. Compositions are available for use in relieving pain and discomfort associated with sunburn. For example, aloe vera gel is often applied to the sunburned skin in an attempt to relieve pain. Many existing compositions, even if they do provide some pain relief, result in other discomfort. For example, typical treatment compositions exhibit a "sticky" sensation once applied to the sunburned skin, which can be uncomfortable, particularly when clothing is worn over the affected skin. In addition, although existing compositions may temporarily relieve pain associated with sunburn, there is often little if any acceleration of the healing process. In effect, such compositions simply ease discomfort during the body's own process for healing the skin. As such, there exists a need for compositions which can relieve pain associated with sunburn, which minimize discomfort, and which preferably may actually accelerate healing, for example by minimizing any tendency of the skin to peel during healing.

SUMMARY OF THE PREFERRED EMBODIMENTS

According to one embodiment, the inventive treatment composition includes an anesthetic component, an anti-inflammatory component, an emollient, and a pharmaceutically acceptable base. The composition may preferably be formulated as a cream, although it may also be possible to formulate the composition as a gel or even a wash that can be applied to the skin. In actual testing, the composition has been found to reduce the necessary healing time, and in the case of sunburn, was found to advantageously prevent or reduce the tendency of the skin to peel.

These and other benefits, advantages and features of the present invention will become more full apparent from the following description and appended claims, or may be learned by the practice of the invention as set forth hereinafter.

DETAILED DESCRIPTION OF THE PREFERRED EMBODIMENTS

I. Introduction

According to one embodiment, the inventive treatment composition includes an anesthetic component, an anti-inflammatory component, an emollient, and a pharmaceutically acceptable base. The composition may preferably be formulated as a cream, although it may also be possible to formulate the composition as a gel or even a wash that can be applied to the skin. As a skin cream, the composition has been found to be helpful in the treatment of burned or irritated skin (e.g., sunburn, razor burn, bug bites, rashes, excema, or even possibly $1^{st}$-$2^{nd}$ degree burns). The composition tends to reduce the necessary healing time, and in the case of sunburn, acts to actually prevent or reduce the tendency of the skin to peel.

An example of a particularly preferred anesthetic component is lidocaine. It is believed that other topical anesthetic components (e.g., benzocaine) may alternatively or additionally be used, although lidocaine has been found to be particularly effective. An example of a particularly preferred anti-inflammatory agent is hydrocortisone. An example of a particularly preferred emollient is aloe vera, which may optionally (and preferably) be combined with jojoba oil. An example of a pharmaceutically acceptable base may include a water-gel carrier or base mixture, as well as additional carriers or solvents (e.g., one or more of ethanol, glycerin, benzyl alcohol, and/or purified water). An example of a suitable water-gel mixture that has been found to be particularly effective is Hawkins Pharmaceutical Vanishing Cream. Additional thickening components (e.g., propylene glycol and/or carbopol 934) may be used depending on the desired consistency of the composition. The use of aloe vera, jojoba oil, and Hawkins Pharmaceutical Vanishing Cream has been found to advantageously provide the composition with a cream like consistency; upon application to the skin, there is no slimy or sticky residue, but the composition becomes nearly dry to the touch.

The amounts of the anesthetic, anti-inflammatory agent, and the emollients may vary somewhat. For example, the anesthetic (particularly lidocaine) is preferably included in an amount between about 0.1% and about 5% by weight, more preferably between about 0.3% and about 2% by weight, and most preferably between about 0.5% and about 1% by weight.

The anti-inflammatory agent (particularly hydrocortisone) is preferably included in an amount between about 0.1% and about 10% by weight, more preferably between about 0.3% and about 5% by weight, and most preferably between about 0.5% and about 1% by weight. either the lidocaine or hydrocortisone may be as high as 5%.

The emollient (particularly aloe vera) is preferably included in an amount between about 1% and about 20% by weight, more preferably between about 2% and about 15% by weight, and most preferably between about 3% and about 10% by weight. Jojoba oil is preferably included in an amount between about 1% and about 20% by weight, more preferably between about 2% and about 15% by weight, and most preferably between about 3% and about 10% by weight. In one particularly preferred embodiment, the aloe vera and jojoba oil are included in equal fractions (e.g., the composition comprises 5% of each). In addition, coconut oil and/or almond oil may be included as soothing and moisturizing agents.

Additional components may be included within the treatment composition. For example, vitamin or herbal components such as *melaleuca alternifolia*, vitamin E, *arnica montana* flower extract, chamomile flower extract, tahitian/hawaiian noni, hawthorne herb, ginger, chamomile (German), beta-carotene, potassium, vitamin A, vitamin B Complexes, vitamin B12, vitamin C, calamine (e.g., a mix of zinc hydroxycarbonates and silicates) caffeine, BAN ZHI LIAN (herba scutellariae barbatae), CE BAI YE (cacumen biotae orientalis), JIU DA BU SHIH, or LU FENG FANG (nidus vespae) may be included within the composition. When included, such vitamin or herbal components may be present within a range from about 0.01 percent to about 5 percent by weight of the composition, more preferably 0.05 percent to about 3 percent by weight of the composition, and most preferably about 0.1 percent to about 2 percent by weight.

Other active components may also be included. For example, trolamine 99 may be included as an analgesic. 1,1,1-trichloro-2-methyl-2-propanol(chlorobutanol) may be included as a preservative and local anesthetic. Benzalkonium chloride (e.g., in a concentration of up to about 0.13% by volume) may be included as an anti-viral/infective component. Silver sulfadiazine may be included as an anti-bacterial/infective component. Zinc may be included as an anti-oxidant to protect against premature skin aging. Zinc oxide may be included to prevent dehydration of the skin. Caffeine may be included as a tanning aid and for skin cancer prevention. When included, such additional active components may be present within a range from about 0.01 percent to about 5 percent by weight of the composition, more preferably 0.05 percent to about 3 percent by weight of the composition, and most preferably about 0.1 percent to about 2 percent by weight.

II. Examples

Example 1

A hypothetical exemplary composition is formed by mixing together the following components:

| | |
|---|---|
| Lidocaine | 0.5-1% |
| Hydrocortisone | 1% |
| Aloe Vera | 5% |
| Jojoba Oil | 5% |
| Ethanol | 4% |
| Glycerin | 10% |
| Benzyl Alcohol | 2% |
| Vanishing Cream | 72% |

Example 2

An exemplary composition was formed by mixing together the following components:

| | |
|---|---|
| Lidocaine Hydrochloride USP Monohydrate | 1 gram |
| Ethanol (95% liquid) | 7 ml |
| Hydrocortisone Acetate USP Micronized Powder | 1 gram |
| *Aloe Vera* (freeze dried powder) | 0.43 gram |
| Jojoba Oil | 4.43 grams |
| Benzyl Alcohol | 2.3 grams |
| Glycerin | 8.6 grams |
| SimpleGel 30 | 5 grams |
| TommyGel | 3 grams |
| Water | 56.4 grams |
| TommyGel Blank Base | 12 grams |

The lidocaine was first dissolved in the ethanol. In an unguator jar, the benzyl alcohol, TommyGel, Water, Hydrocortisone Acetate, and Aloe Vera were mixed together. The lidocaine-ethanol solution was added to the jar and mixed. The jojoba oil, SimpleGel 30, and glycerin are added to the jar and mixed again. The TommyGel Blank Base is finally added and mixed. The resulting composition has a cream like consistency. Upon application to the skin, there is no slimy or sticky residue, but the composition becomes nearly dry to the touch. It exhibits a smooth, silk like feel once applied. When applied to an area of burned or irritated skin, the pain immediately subsided, and in the case of sunburn, there was a noticeable tendency for the composition to reduce or eliminate peeling of the skin as the sunburn healed.

Example 3

A hypothetical exemplary composition is formed by mixing together the following components:

| | |
|---|---|
| Lidocaine | 1 gram |
| Ethanol | 4 ml |
| Hydrocortisone | 1 gram |
| *Aloe Vera* (freeze dried powder) | 0.5 gram |
| Jojoba Oil | 5 ml |
| Benzyl Alcohol | 2 ml |
| Glycerin | 10 ml |
| Vanishing Cream Base | q.s. 100 grams |

The composition is mixed as in Example 2. The resulting composition has a cream like consistency. Upon application to the skin, there is no slimy or sticky residue, but the composition becomes nearly dry to the touch. It exhibits a smooth, silk like feel once applied. When applied to an area of burned or irritated skin, the pain immediately subsides, and in the case of sunburn, there is a noticeable tendency for the composition to reduce or eliminate peeling of the skin as the sunburn heals.

Example 4

Because of FDA regulatory issues, it may be desireable to provide treatment compositions that include either the anesthetic component or the anti-inflammatory component, but not both (e.g., for over the counter sale). Such compositions are presented in Examples 4 and 5. A hypothetical exemplary composition is formed by mixing together the following components:

| | |
|---|---|
| Ethanol | 4 ml |
| Hydrocortisone | 1 gram |
| *Aloe Vera* (freeze dried powder) | 0.5 gram |

-continued

| | |
|---|---|
| Jojoba Oil | 5 ml |
| Benzyl Alcohol | 2 ml |
| Glycerin | 10 ml |
| Vanishing Cream Base | q.s. 100 grams |

The composition is mixed as in Example 3, except it includes no lidocaine. The resulting composition has a cream like consistency. Upon application to the skin, there is no slimy or sticky residue, but the composition becomes nearly dry to the touch. It exhibits a smooth, silk like feel once applied.

Example 5

A hypothetical exemplary composition is formed by mixing together the following components:

| | |
|---|---|
| Ethanol | 4 ml |
| Lidocaine | 1 gram |
| *Aloe Vera* (freeze dried powder) | 0.5 gram |
| Jojoba Oil | 5 ml |
| Benzyl Alcohol | 2 ml |
| Glycerin | 10 ml |
| Vanishing Cream Base | q.s. 100 grams |

The composition is mixed as in Example 3, except it includes no hydrocortisone. The resulting composition has a cream like consistency. Upon application to the skin, there is no slimy or sticky residue, but the composition becomes nearly dry to the touch. It exhibits a smooth, silk like feel once applied.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A composition for the treatment of sunburned skin consisting of:
    an anesthetic component consisting of lidocaine, the lidocaine consisting between about 0.5% and about 1% by weight of the composition;
    an anti-inflammatory component consisting of hydrocortisone, the hydrocortisone consisting between about 0.5% and about 1% by weight of the composition;
    an emollient consisting of approximately equal fractions aloe vera and jojoba oil, the aloe vera and jojoba oil each consisting between about 3% and about 10% by weight of the composition; and
    a pharmaceutically acceptable base, wherein the pharmaceutically acceptable base consists of components selected from the group consisting of ethanol, glycerin, benzyl alcohol, purified water, and mixtures thereof.

2. A composition for the treatment of sunburned skin consisting of:
    an anesthetic component consisting of lidocaine, the lidocaine consisting between about 0.5% and about 1% by weight of the composition;
    an anti-inflammatory component consisting of hydrocortisone, the hydrocortisone consisting between about 0.5% and about 1% by weight of the composition;
    an emollient consisting of aloe vera and jojoba oil, the aloe vera and jojoba oil each consisting between about 3% and about 10% by weight of the composition; and
    a pharmaceutically acceptable base, wherein the pharmaceutically acceptable base consists of components selected from the group consisting of ethanol, glycerin, benzyl alcohol, purified water, and mixtures thereof.

3. A composition as recited in claim 2, wherein the aloe vera and jojoba oil are each present in an amount of about 5% by weight of the composition.

4. A composition for the treatment of sunburned skin consisting of:
    an anti-inflammatory component consisting of hydrocortisone, the hydrocortisone consisting between about 0.5% and about 1% by weight of the composition;
    an emollient consisting of aloe vera and jojoba oil, the aloe vera and jojoba oil each consisting between about 3% and about 10% by weight of the composition; and
    a pharmaceutically acceptable base, wherein the pharmaceutically acceptable base consists of components selected from the group consisting of ethanol, glycerin, benzyl alcohol, purified water, and mixtures thereof.

5. A composition for the treatment of sunburned skin consisting of:
    an anesthetic component consisting of lidocaine, the lidocaine consisting between about 0.5% and about 1% by weight of the composition;
    an emollient consisting of aloe vera and jojoba oil, the aloe vera and jojoba oil each consisting between about 3% and about 10% by weight of the composition; and
    a pharmaceutically acceptable base, wherein the pharmaceutically acceptable base consists of components selected from the group consisting of ethanol, glycerin, benzyl alcohol, purified water, and mixtures thereof.

* * * * *